United States Patent
Drieu

(10) Patent No.: US 6,274,621 B1
(45) Date of Patent: *Aug. 14, 2001

(54) GINKGOLIDES FOR INHIBITION OF MEMBRANE EXPRESSION OF BENZODIAZEPINE RECEPTORS

(75) Inventor: Katy Drieu, Paris (FR)

(73) Assignee: Societe de Conseils de Recherches et d'Applications Scientifiques, SAS, Paris (FR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/068,368
(22) PCT Filed: Nov. 8, 1996
(86) PCT No.: PCT/EP96/05005
  § 371 Date: Jul. 23, 1998
  § 102(e) Date: Jul. 23, 1998
(87) PCT Pub. No.: WO97/17068
  PCT Pub. Date: May 15, 1997

Related U.S. Application Data

(63) Continuation-in-part of application No. 08/575,902, filed as application No. PCT/EP96/05005 on Nov. 8, 1996, now abandoned.
(60) Provisional application No. 60/007,337, filed on Nov. 9, 1995.

(51) Int. Cl.$^7$ .................................................. A61K 31/34
(52) U.S. Cl. ........................................................... 514/468
(58) Field of Search ............................................. 514/468

(56) References Cited

U.S. PATENT DOCUMENTS 5,346,894  9/1994  Korth ................................. 514/220

FOREIGN PATENT DOCUMENTS

WO 95/18131  7/1995  (WO).

OTHER PUBLICATIONS

Rote Liste 1994 (36001–36012) with English Translation.*
Petkov et al., "Effects of Standardized Extracts GK501, from Ginkgo Biloba L., G115 from Panax ginseng C.A. Meyer, and their Combination, Gincosan (PHL–00701), on the Brain Levels of Biogenic Monamines and on the Serum Content of Prolactin, Growth Hormone and ACTH", Phytotherapy Research, 7:139–145 (1993).*

Bruel et al., "Effects of Ginkgo Biloba Extract on Glucose Transport and Glycogen Synthesis of Cultured Smooth Muscle Cells from Pig Aorta", Pharmacoloigcal Res. 21:421–429, 1989.

Oliver et al., "Effect of Ginkgo Biloba Extract on the Hypothalamo–Pituitary–Adrenal Axis and Plasma Catecholamines Levels in Stress", Eur J. Endocrinol 130. Suppl 2, P3.072, 1994.

Porsolt et al., "Effects of an Extract of Ginkgo Biloba (EGB 761) on "Learned Helplessness" and Other Models of Stress in Rodents", Pharmacology Biochemistry & Behavior 36:963–971, 1990.

Rapin et al., "Demonstration of the "Anti–Stress" Activity of an Extract of Ginkgo Biloba (EGb 761) Using a Discrimination Learning Task", Gen. Pharmac. 25:1009–1016, 1994.

Rapin et al., "Effects of Repeated Treatments With an Extract of Ginkgo Biloba (EGb 761) and Bilobalide on Glucose Uptake and Glycogen Synthesis in Rat Erythrocytes:An Ex Vivo Study", Drug Devel. Res. 31:164–169, 1994.

Rodrigez De Turco et al., "EGb 761 Inhibits Stress–Induced Polydipsia in Rats", Physiology & Behavior 53:1001–1002, 1993.

Vasseur et al., "Effects of Repeated Treatments with an Extract of Ginkgo Biloba (EGb 761), Bilobalide and Ginkgolide B . . . ", Gen. Pharmac 25:31–46, 1994.

Bernardini, R. et al., Endocrinology 125 (2), 1067–1073, 1989.

Blasquez, C. et al., Eur J Pharmacol 177 (3), 145–154, 1990.

* cited by examiner

Primary Examiner—William R. A. Jarvis
(74) Attorney, Agent, or Firm—Brian R. Morrill; John D. Conway; Fish & Richardson

(57) ABSTRACT

This invention relates to the use of ginkgolides and extracts of Ginkgo biloba for inhibiting the membrane expression of benzodiazepine receptors and for inhibiting the release of glucocorticoids in a patient.

12 Claims, No Drawings

GINKGOLIDES FOR INHIBITION OF MEMBRANE EXPRESSION OF BENZODIAZEPINE RECEPTORS

CROSS REFERENCE TO RELATED APPLICATIONS

This application is a 35 U.S.C. 371 filing of International Application Number PCT/EP96/05005 filed Nov. 8, 1996, which is a continuation-in-part of U.S. application Ser. No. 08/575,902, filed Dec. 20, 1995, now abandoned, which is a continuation-in-part of and claims priority from provisional application No. 60/007,337, filed Nov. 9, 1995, now abandoned.

FIELD OF THE INVENTION

The invention relates to the inhibition of membrane expression of benzodiazepine receptors and in particular to the use of ginkgolides for the manufacture of medicaments for such membrane expression inhibition.

BACKGROUND OF THE INVENTION

The steroid glucocorticoid is produced by adrenal fasciculata-reticula cells in the adrenal glands, and are secreted in response to an increase in the level of plasma adrenocorticotrophic hormone (ACTH). Glucocorticoids are involved in carbohydrate, protein, and fat metabolism, have been shown to have anti-inflammatory properties, and are hypersecreted during stress. In excess, glucocorticoids have been shown to damage hippocampus, a structure in the limbic system of the brain that is critical to cognitive functions such as learning and memory. See, e.g., Sapolsky, R. M., Ann. N.Y. Acad. Sci. 746:294 (1994); and McEwen, B. S., Ann. N.Y. Acad. Sci. 746:134 (1994). Furthermore, glucocorticoid neurotoxicity and neuroendangerment has been shown to be critical in neural development and aging as well as in neurological diseases related to hippocampal damage. See, e.g., deKloet, E. R., et al., Ann. N.Y. Acad. Sci. 746:8 (1994).

Studies have been conducted to examine the beneficial effects of extract of the leaves of the gymnosphermus tree ginkgo biloba (e.g., EGb 761) on "antistress" activity by lowering corticosterine levels in stressed rat models. See, Rapin, et al., Gen. Pharmac. 25(5):1009 (1994). EGb 761 had previously been shown to have activity in the cardiovascular system (e.g., reduction of platelet adhesion and thrombi growth), central nervous system (e.g., neuroprotective activity), and neurosensory system (e.g., retinal protection). See, e.g., DeFeudis, et al., Ginkgo Biloba Extract (EGb 761): Pharmaceutical Activities and Clinical Applications (Elsevier, Paris, 1991).

It has now been found that ginkgolides are effective at inhibiting membrane expression of benzodiazepine receptors, eg. adrenal benzodiazepine receptors, and that, having this effect, they can be used to inhibit glucocorticoid release.

SUMMARY OF THE INVENTION

Thus viewed from one aspect the invention provides the use of a ginkgolide for the manufacture of a medicament for use as an inhibitor of membrane expression of a benzodiazepine receptor, eg. to inhibit glucocorticoid release in a patient. Alternatively viewed the invention provides the use of an inhibitor of membrane expression of an adrenal benzodiazepine receptor, eg. a ginkgolide, for the manufacture of a medicament for inhibiting glucocorticoid release, eg. to combat (ie. prevent or treat) conditions associated with excess glucocorticoid production.

Viewed from a further aspect the invention provides a pharmaceutical composition for use as an inhibitor of membrane expression of benzodiazepine receptors (or for combatting conditions associated with excess glucocorticoid production, etc.), said composition comprising a physiologically tolerable ginkgolide together with at least one pharmaceutically acceptable carrier or excipient.

Viewed from a yet further aspect the invention provides a pharmaceutical composition for use as an inhibitor of glucocorticoid release, said composition comprising an inhibitor of membrane expression of an adrenal benzodiazepine receptor (eg. a ginkgolide) together with at least one pharmaceutically acceptable carrier or excipient.

Viewed from a yet still further aspect the invention provides a method of inhibiting the membrane expression of a benzodiazepine receptor in a patient (eg. a human or non-human, preferably a mammal), said method comprising administering to said patient an effective amount of a ginkgolide. Viewed from a still further aspect the invention provides a method of inhibiting the release of a glucocorticoid in a patient, said method comprising administering to said patient an effective amount of a compound, eg. a ginkgolide, capable of inhibiting the membrane expression of an adrenal benzodiazepine receptor.

Reduction in excess glucocorticoid levels can, as discussed below, result in enhancement of ACTH levels with various consequent beneficial effects.

Thus viewed from a still further aspect the invention also provides the use of a ginkgolide (or other inhibitor of membrane expression of an adrenal benzodiazepine receptor) for the manufacture of a medicament for enhancing ACTH levels.

Thus one aspect of the invention involves inhibiting the membrane expression of a benzodiazepine receptor. This involves administering to a patient an effective amount of a ginkgolide. The benzodiazepine receptor may be a peripheral-type benzodiazepine receptor (PBR), e.g. found on the adrenal, intestine, kidney, brain, liver, and testis. In one embodiment, the membrane is on adrenal mitochondria. In a further embodiment, this method comprises administering an effective amount of an extract from ginkgo biloba. In another further embodiment this method comprises administering an effective amount of a pharmaceutical composition which contains a ginkgolide and a pharmaceutically acceptable carrier.

However another aspect of the invention involves inhibiting the release of a glucocorticoid (such as cortisol) in a patient. This involves the step of administering to the patient an effective amount of a compound capable of inhibiting the membrane expression of an adrenal benzodiazepine receptor. In one embodiment, this method comprises administering to said patient an effective amount of a ginkgolide. In a further embodiment, this method comprises administering an effective amount of an extract from ginkgo biloba. In another further embodiment, this method comprises the step of administering to the patient an effective amount of a pharmaceutical composition containing a ginkgolide and a pharmaceutically acceptable carrier.

An effective amount depends upon the condition being treated, the route of administration chosen, and the specific activity of the compound used, and ultimately will be decided by the attending physician or veterinarian. The compound may be administered in an amount of 0.1 to 20 mg/kg body weight of the patient (e.g., 0.5 to 4 mg/kg body weight of the patient).

The pharmaceutical composition described above contains (1) one or more of the ginkgolides to be described below, (2) one or more pharmaceutically acceptable carriers, and, optionally, (3) one or more other ingredients such as another bioactive compound or a stabilizing agent. Any extract from the ginkgo biloba tree is not considered as such a pharmaceutical composition. The carrier must be "pharmaceutically acceptable" in the sense of being compatible with the ginkgolide(s) of the composition and not deleterious to the subject to be treated.

The compositions may conveniently be presented in unit dosage form and may be prepared by any of the methods well known in the art of pharmacy. All methods include the step of bringing the compound(s) (e.g., ginkgolide) into association with a carrier which may contain one or more accessory ingredients. In general, the compositions for tablets (e.g., for oral administration) or powders are prepared by uniformly and intimately blending the compound(s) with finely divided solid carriers, and then, if necessary as in the case of tablets, forming the product into the desired shape and size.

Compositions suitable for parenteral administration (e.g., subcutaneous, intravenous, or intermuscular), on the other hand, conveniently comprise sterile aqueous solutions of the compound(s). Preferably, the solutions are isotonic with the blood of the subject to be treated. Such compositions may be conveniently prepared by dissolving solid compound(s) in water or saline to produce an aqueous solution, and rendering said solution sterile. The composition may be presented in unit or multi-dose containers, for example, sealed ampoules or vials.

The extracts of the ginkgo biloba tree may be prepared by standard extraction techniques. See, e.g., the book, "*Ginkgolides—Chemistry,* Biology, Pharmacology and Clinical Perspectives", edited by P. Braquet (J. R. Prous, Science Publishers, Barcelona, Spain 1988).

Other features and advantages of the present invention will be apparent from the detailed description of the invention and from the claims.

DETAILED DESCRIPTION OF THE INVENTION

It is believed that one skilled in the art can, based on the description herein, utilize the present invention to its fullest extent. The following specific embodiments are, therefore, to be construed as merely illustrative, and not limitative of the remainder of the disclosure in any way whatsoever.

Unless defined otherwise, all technical and scientific terms used herein have the same meaning as commonly understood by one of ordinary skill in the art to which this invention belongs. Also, all publications cited herein are incorporated by reference.

Ginkgolides

The term "ginkgolide" are used herein to include all the naturally occurring ginkgolides which are derived from the ginkgo biloba tree as well as synthetically produced ginkgolides and pharmaceutically active derivatives and salts thereof. Thus, it includes (1) the various ginkgolides disclosed in the books "Ginkgolides—Chemistry, Biology, Pharmacology and Clinical Perspectives", edited by P. Braquet (J. R. Prous, Science Publishers, Barcelona, Spain 1988); F. V. DeFeudis, Ginkgo Biloba Extract (EGb 761), Pharmacological Activities and Chemical Applications (Elsevier, Paris, France 1991); Rokan Ginkgo Biloba—Recent Results in Pharmacology and Clinic, edited by E. W. Feufgeld (Springer-Verlag, Berlin, Germany 1988) and in U.S. Pat. Nos. 4,734,280 and 5,002,965; and (2) non-toxic, pharmaceutically active derivatives thereof such as 2,3-dehydro, 1-methoxy, and 1-ethoxy derivatives of ginkgolide B, tetrahydro ginkgolide derivatives, acetyl ginkgolide derivatives, and alkyl ester of ginkgolide, e.g., the monoacetate ginkgolide derivatives described in Okabe, et al., J. Chem. Soc.(C) pp. 2201–2206 (1967); and Corey, et al., J. Amer. Chem. Soc. 110:649 (1988).

As described in the book "Ginkgolides—Chemistry, Biology, Pharmacology and Clinical Perspectives", pp. 27–42, edited by P. Braquet (J. R. Prous, Science Publishers, Barcelona, Spain 1988), ginkgolides may be extracted and purified from the leaves of the ginkgo biloba tree. See, e.g., Okabe, J. Chem. Soc. (C) pp. 2201 (1967); and Nakanishi, Pure & Applied Chem. 14:89 (1967). Ginkgolides and ginkgolide derivatives have also been chemically synthesized. See, e.g., Corey, et al., J. Amer. Chem. Soc. 110:649 (1988). Furthermore, ginkgolides are available from various commercial sources such as Sigma Chemical (St. Louis, Mo., U.S.A.).

Structurally, ginkgolides are twenty carbon molecules with 6 five-membered rings joined together to form a constrained structure which incorporates a t-butyl group. Of the 6 rings, 3 are lactone rings, 2 are carboxylic rings joined by a single carbon to form a spiro-[4,4]nonane ring system, and 1 tetrahydrofuran ring. Examples of ginkgolides are depicted by the following formula:

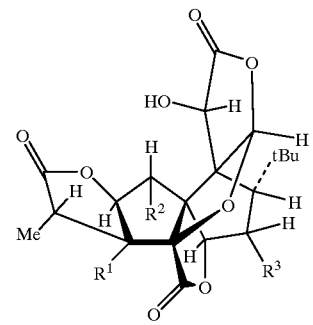

wherein each of $R^1$, $R^2$, and $R^3$, independently, is H, OH, or $C_1$–$C_6$ alkoxy, or a pharmaceutically acceptable salt thereof. Examples of ginkgolides include ginkgolide A ($R^1$=OH, $R^2$=H, $R^3$=H), ginkgolide B ($R^1$=OH, $R^2$=OH, $R^3$=H), ginkgolide C ($R^1$=OH, $R^2$=OH, $R^3$=OH), ginkgolide J ($R^1$=OH, $R^2$=H, $R^3$=OH), and ginkgolide M ($R^1$=H, $R^2$=OH, $R^3$—OH) or the synthetic analogs where $R^2$ is $C_1$–$C_6$ alkoxy, e.g., 1-methoxy or 1-ethoxy derivatives of ginkgolide B. The term "ginkgolide" also includes all pharmaceutically acceptable salts of ginkgolides, such as sodium, potassium, and magnesium salts thereof. Examples of a ginkgolide to be used to practice the method of this invention has the above formula, in which each, $R^1$ and $R^3$, independently, is H or OH, and $R^2$ is H, OH, or $C_1$–$C_6$ alkoxy (such as ginkgolides A, B, C, J, and M); or a pharmaceutically acceptable salt thereof.

Benzodiazepine Radioligand Binding Assay

The ginkgo biloba extract EGb761, ginkgolide A, and ginkgolide B (Institut Henri Beaufour-IPSEN, Paris, France) were tested for their ability to decrease the number of binding sites for the peripheral benzodiazepine receptor ligand PK 11195, which binds to an 18 Kd peripheral benzodiazepine receptor protein, in adrenal mitochondria. See, Garnier, et al., Endocrinology 132:444 (1993). Mitochondria were prepared as described in Krueger, et al., J. Biol. Chem. 265:15015 (1990). Mitochondria (50 mg of protein) were resuspended in phosphate buffered saline (PBS) and [$^3$H]PK 11195 (New England Nuclear, Wilmington, Del., U.S.A.). Binding studies were performed at 4° C. in a final incubation volume of 0.3 ml, using radioligand in the concentration range of 0.019–20.00 nM and 200 fold excess of unlabeled PK 11195 (Research Biochemicals, Natick, Mass., U.S.A.), as described in Garnier, et al., Endocrinology 132:444 (1993) and Garnier, et al., Mol. Pharm. 45:201 (1994). After 120 min. incubation time, the assay was stopped by filtration through Whatman GF/C filters and washed with 15 ml ice-cold PBS. Radioactivity trapped on the filters were determined by liquid scintillation counting at 50% counting efficiency. The dissociation constant (Kd) and the number of binding sites (Bmax) were determined by Standard plot analysis of the data using the ligand™ program (Kell, V.4.0, Biosoft, Inc.). See Munson, et al., Anal. Biochem. 107:220 (1980). The results are shown below in Table I.

TABLE I

|  | Kd (nM) | Bmax (pmol/mg) |
|---|---|---|
| Control | 1.7 | 11.2 |
| EGb761 | 1.2 | 7.1 |
| Ginkgolide A | 1.3 | 5.6 |
| Ginkgolide B | 1.5 | 3.1 |

Thus, EGb761 decreased the expression of the 18 Kd peripheral benzodiazepine receptor protein by 40%, while ginkgolide A and ginkgolide B reduced the expression by 50% and 73%, respectively.

This finding was verified by immunocytochemical studies using antisera specific for the 18 Kd peripheral benzodiazepine receptor protein. See Oke, et al., Mol. Cell. Endocrinol. 87:R1 (1992) and Garnier, et al., Endocrinology 132:444 (1993). A dramatic decrease in the protein expression was observed after treatment with EGb761, ginkgolide A, and ginkgolide B.

Immunoblot Analysis of Benzodiazepine Receptor

The ginkgolide induced decrease in the 18 Kd peripheral benzodiazepine receptor protein was also confirmed by immunoblot analysis of mitochondrial extracts obtained from control and treated animals. Adrenal mitochondrial proteins were fractioned by one dimension SDSPAGE and electro-transferred onto nitrocellulose as described in Oke, et al., Mol. Cell. Endocrinol. 87:R1 (1992) and Garnier, et al., Endocrinology 132:444 (1993). The nitrocellulose was subjected to immunoblot analysis using anti-peripheral benzodiazepine receptor antibody and goat IgG-horseradish peroxidase with 4-chloro-1-napthol as color reagent and hydrogen peroxide as substrate. Densiometric analysis of the immunoreactivity protein bonds was performed using Sigmagel™ software (Jandel Scientific, San Rafael, Calif., U.S.A.). The densiometric analysis of the immunoreactivity found a 60% decrease of the 18 Kd peripheral benzodiazepine receptor protein by ginkgolide B.

mRNA Expression of Benzodiazepine Receptor

The ginkgolide induced decrease in mRNA expression of the benzodiazepine receptor was also confirmed. Total cellular RNA from adrenal tissue was isolated by the acid guanidinium thiocyanate-phenol-chloroform extraction method (Chomczynski, et al., Anal. Biochem. 162:156–159 (1987)) using the RNAzol B reagent (Tel-Test Inc., Friendswood, Tex., U.S.A.). RNA electrophoresis transfer, probe labelling, and membrane hybridization were performed as previously described in Dym, et al., Endocrinology 128:1167–1176 (1991). RNA was size-fractionated by electrophoresis and transferred to derivatized nylon membranes (Nytran Plus, Schleicher & Schuell, Keene, N.H., U.S.A.). The blots were then hybridized against the [$^{32}$p] cDNA probe for PBR labelled by the random priming technique. The 781 base-pair probe for PBR mRNA used was prepared as previously described in Garnier, et al., Endocrinology 132:444–458 (1993). Screen enhanced autoradiography was performed by exposing Kodak X-OMAT AR films to the blots at −80° C. for 48 hours. Densiometric analysis of the spots was performed as described above. Both EGb761 and ginkgolide B treatment was found to reduce peripheral benzodiazepine receptor mRNA expression by 50% and 85%, respectively.

Assay for Determining the Inhibition of Glucocorticoids

Adult Sprague-Dawley rats (approximately 300 g; Charles River Laboratories, Wilmington, Mass., U.S.A.) were treated once daily for eight days with either ginkgolide A, ginkgolide B, or a saline control. Ginkgolide A and ginkgolide B were injected as an aqueous solution intraperitoneally at a 2 mg/kg. The results shown in Table II are the means of between two to four independent experiments. In each experiment, at least six rats per treatment group were used. After eight days of treatment, the rats were sacrificed.

The level of steroids in the rats was measured by radioimmunoassay from organic extracts of the collected serum. The levels of corticosterone (a glucocorticoid in rats) and testosterone were measured by radioimmunoassay using antibodies from Endocrine Sciences (Tarlana, Calif., U.S.A.) under conditions described by the supplier. The level of plasma ACTH was measured by radioimmunoassay using the method of Crousos, et al., New Engl. J. Med. 310:622 (1984). The level of aldosterone was measured by radioimmunoassay using a kit from Diagnostics Products Corp. (Los Angeles, Calif., U.S.A.). The mean steroid levels for each of the four treatment groups are reported in Table II.

TABLE II

| TREATMENT | CORTI-COSTER-ONE ng/ml | ACTH pg/ml | ALDOSTER-ONE pg/ml | TESTOS-TERONE ng/ml |
|---|---|---|---|---|
| Control | 161 | 28.0 | 685 | 4.50 |
| Ginkgolide A | 66 | 103 | 638 | 4.75 |
| Ginkgolide B | 75 | 71.4 | 883 | 4.50 |

Ginkgolide A and ginkgolide B were all found to decrease the level of corticosterone in the rats. Because glucocorticoid secretion induced by the pituitary ACTH is modulated by a negative feedback system on the hypothalamus, the decrease in corticosteroid levels in the rats as a result of the administration of ginkgolide A and ginkgolide B will induce a corresponding increase in pituitary ACTH release and, consequently, plasma ACTH levels.

As shown in Table II, treatment with either ginkgolide A or ginkgolide B was found unexpectedly to cause the rats to naturally respond and increase ACTH release. Furthermore, serum levels of aldosterone (secreted by the adrenal cortex) and testosterone (secreted by the testes) were unaffected by the treatment of ginkgolide A and ginkgolide B, indicating that ginkgolides specifically affect the adrenal fasciculata-reticular cells of the adrenal gland.

Use

By inhibiting the release of glucocorticoids from the adrenal glands, ginkgolides can be used to treat disorders in patients that are secreting a high level of one or more glucocorticoids. Examples of such patients include those suffering from Cushings syndrome and those with stress-induced hypercorticolism. As discussed above, the levels of ACTH are naturally elevated in response to the suppression of glucocorticoid release upon administration of a ginkgolide. Elevated levels of ACTH or ACTH analogs have been shown to inhibit brain aging (e.g., inhibit neurological loss and improve learning). See, e.g., Laudfield, et al., Science, 214:581 (1981). Thus, ginkgolides enhance brain function by both inhibiting glucocorticoid and maintaining normal ACTH release.

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A method of inhibiting the membrane expression of a benzodiazepine receptor in a patient, said method comprising administering to said patient an effective amount of a ginkgolide.

2. A method of claim 1, wherein said benzodiazepine receptor is the peripheral-type benzodiazepine receptor.

3. A method of claim 1, wherein said membrane is on adrenal mitochondria.

4. A method of inhibiting the release of a glucocorticoid in a patient, said method comprising administering to said patient an effective amount of a ginkgolides or ginkgo biloba extracts capable of inhibiting the membrane expression of an adrenal benzodiazepine receptor.

5. A method of claim 4, wherein said method comprises administering to said patient an effective amount of a ginkgolide.

6. A method of claim 4, wherein said glucocorticoid is cortisol and said patient is human.

7. A method of claim 1, wherein said method comprises administering an effective amount of an extract from ginkgo biloba.

8. A method of claim 1, wherein said method comprises administering an effective amount of a pharmaceutical composition which contains a ginkgolide and a pharmaceutically acceptable carrier.

9. A method of claim 8, wherein said ginkgolide is of formula I

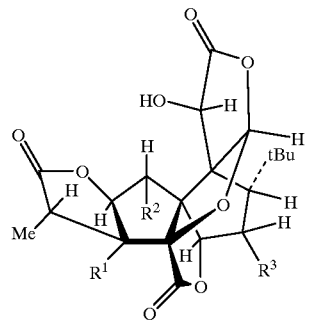

(wherein each $R^1$ and $R^3$, independently, is H or OH, and $R^2$ is H, OH, or $C_1$–$C_6$ alkoxy) or a pharmaceutically acceptable salt thereof.

10. A method of claim 9, wherein said ginkgolide is a compound of formula I wherein $R^1$ is OH, $R^2$ is H or OH, and $R^3$ is H, or a pharmaceutically acceptable salt thereof.

11. A method of claim 1, wherein administration is effected parenterally.

12. A method of claim 1, wherein administration is effected orally.

* * * * *